United States Patent [19]
Sarangapani

[11] Patent Number: 5,877,243
[45] Date of Patent: Mar. 2, 1999

[54] ENCRUSTATION AND BACTERIAL RESISTANT COATINGS FOR MEDICAL APPLICATIONS

[75] Inventor: Shantha Sarangapani, Walpole, Mass.

[73] Assignee: ICET, Inc., Norwood, Mass.

[21] Appl. No.: 851,306

[22] Filed: May 5, 1997

[51] Int. Cl.⁶ .............................. C08K 3/10; C08K 5/10; C08K 5/09; C08K 5/51
[52] U.S. Cl. ..................... 524/139; 524/239; 524/291; 524/310; 524/403; 524/413; 524/589; 524/590; 524/871; 524/874; 523/105
[58] Field of Search ..................... 524/589, 590, 524/871, 874, 139, 239, 291, 310, 403, 413; 523/105, 106

[56] References Cited

U.S. PATENT DOCUMENTS

| | | | |
|---|---|---|---|
| 3,798,750 | 3/1974 | Niedrich | 29/570 |
| 4,579,554 | 4/1986 | Glassman | 604/102 |
| 4,642,104 | 2/1987 | Sakamoto et al. | 604/264 |
| 4,878,901 | 11/1989 | Sachse | 604/174 |
| 4,932,948 | 6/1990 | Kemes et al. | 604/349 |
| 4,946,449 | 8/1990 | Davis, Jr. | 604/256 |
| 4,950,256 | 8/1990 | Luther et al. | 604/265 |
| 5,295,979 | 3/1994 | DeLaurentis et al. | 604/265 |
| 5,322,520 | 6/1994 | Milder | 604/265 |
| 5,328,954 | 7/1994 | Sarangapani | 524/589 |

OTHER PUBLICATIONS

Johnson, J.R. et al., "Prevention of Catheter–Associated Urinary Tract Infection with a Silver Oxide–Coated Catheter: Clinical and Microbiologic Correlates," *The Journal of Infectious Diseases* 1990; 162:1145–1150.

Liedberg et al., "Silver Alloy Coated Catheters Reduce Catheter–associated Bacteriuria," *British Journal of Urology* (1990) 65:379–381.

McLean, R.J.C. et al., "Antibacterial activity of multilayer silver–copper surface films on catheter material," *Can. J. Microbiol.* vol. 39, 1993, 895–899.

McLean, R.J.C. et al., "A simple technique for studying struvite crystal growth in vitro," *Urological Research* (1990) 18:39–43.

Nickel, J.C. et al., "Tobramycin Resistance of *Pseudomonas aeruginosa* Cells Growing as a Biofilm on Urinary Catheter Material," *Antimicrobial Agents and Chemotherapy*, Apr. 1985, vol. 24, No. 4, pp. 619–624.

Sarangapani, S. et al., "An improved model for bacterial encrustation studies," *Journal of Biomedical Materials Research*, vol. 29, 1185–1191 (1995).

Schaeffer, A.J. et al., "Effect of Silver Oxide/Trichloroisocyanuric Acid Antimicrobial Urinary Drainage System on Catheter–Associated Bacteriuria," *The Journal of Urology*, vol. 139, January, pp. 69–73.

Webb, C.L. et al., "Aminodiphosphate or $Al^{+++}$ Preincubation Inhibits Calcification of Aortic Homografts in the Rat Subdermal Model," vol. XXXIV *Trans Am Soc Artif Intern Organs 1988*, pp. 851–859.

Primary Examiner—Kriellion S. Morgan
Attorney, Agent, or Firm—Hale and Dorr LLP

[57] ABSTRACT

Disclosed are coatings and materials that resist bacterial colonization and encrustation for use in medical devices and urological applications. The coating includes acidic chelating components, reactively bound to a hydrophilic polyurethane prepolymer along with noble metal combinations or antibacterials. The acidic and noble metal combinations can also be incorporated as additives during plastic molding of medical devices. A continuous antibacterial surfaces are provided by such coatings and materials.

22 Claims, 6 Drawing Sheets

ENCRUSTATION AND BACTERIAL RESISTANT COATINGS FOR MEDICAL APPLICATIONS

BACKGROUND OF THE INVENTION

This invention relates to medical devices that are resistant to bacterial growth or encrustation such as urological devices and more particularly to urinary catheters constructed of, or coated with, a material which enables the urinary catheters to inhibit urease, and to prevent calcium and magnesium phosphate deposits on the catheters.

Urinary catheters are used in urological surgery and when other methods of managing urinary incontinence fail. These catheters are generally made from a non-toxic, non-irritating material which is flexible but which will withstand collapse. Ideally they should resist colonization by bacteria and encrustation by mineral deposits. Short-term urological devices used to control incontinence such as the plastic urethral inserts suffer from susceptibility to bacterial adherence causing Urinary tract infection. (UTI).

The most common materials used for the catheters are latex, plastic or silicone. All biomaterials, including the most recently tested polyurethane, polyurethane-carbon and silicone-carbon, become encrusted with mineral deposits to varying extents. The degree of encrustation formation on biomaterials exposed to urine is dependent upon the biomaterial, the length of urinary exposure, the presence of infection and the solute content of urine. Several independent studies (e.g. Hukins et al., 1989) of the scraped encrusted material have identified—two major salts, namely apatite $Ca_5 (PO_4)_3 (OH)$ and struvite $Mg\ NH_4PO_4\ 6H_2O$. A very small amount of brushite $CaHPO_4.2H_2O$ has also been identified.

The pH increase of urine occurs due to urease producing bacteria, that infect the urine. Urease catalyzes the hydrolysis of urea at an enormous rate ($10^{14}$ times as fast as the spontaneous hydrolysis of urea which is not observable in neutral solution) producing ammonia, which in turn precipitates calcium phosphates.

Microbial heterogeneity and structural complexity of the bio-films observed on infected catheter materials by means of scanning and transmission electron microscopy reveal a variety of microflora. It appears that the adherent microcolonies of bacteria are much less susceptible than their planktonic counterparts to antibiotics because the extensive anionic matrix surrounding the cell appears to comprise an ion exchange barrier between charged antibiotic molecules and their cellular targets. Antibiotics should be reserved for symptomatic, febrile infections; otherwise their use produces a change in bacterial flora with the potential for producing resistance.

Bacteriurea in a catheterized patient indicates the urinary tract has become colonized or infected. Administration of anti-bacterials such as nitrofurantoin, methenamine, and naldixic acid are used in practice. Most of these are not very effective in alkaline urine, and to achieve a high concentration in urine, the patient has to be given enormous doses.

Catheter associated Bacteriurea results from ascending bacterial colonization within glycocalyx enclosed biofilm on the inside and/or outside surfaces of the catheter and drainage systems. Urinary tract catheters made from a biomaterial that inhibits bacterial adherence and thus retards upstream colonization of bacteria may reduce acquired urinary tract infection (UTI). While hydrophilic surfaces show reduced protein adhesion, antibacterial surfaces offer better protection. Either a controlled release or an antibacterial immobilized on the surface should offer continuous protection against bacterial colonization. A silver oxide catheter is described in a publication by Shaeffer, A. J., Story, K. O., Johnson, S. M. in "Effect of silver oxide/Trichloroisocyanuric Acid Antimicrobial Urinary Drainage System on Catheter Associated Bacteriurea", J. Urol., 39, 60 (1988). A recent clinical study on silver catheters reported by Johnson, J. R., Roberts, P. L., Olsen, R. J., Moyer, K. A., and Stanni, W. E. in "Silver Oxide Coated Catheters", J. Infect. Diseases, 162, 1145 (1990) indicated the prevention of UTI among women not receiving antimicrobials.

The other problem associated with catheters left in place for long periods of time is the encrustation due to the formation of calcium hydroxyapatite and struvite. Long-term urethral catheterization is frequently necessary for patients with intractable urinary incontinence or retention. This procedure is employed in as many as 16–28% of patients in various chronic care facilities. More than 50% could suffer from blockage of their catheters. This can cause incontinence due to urinary bypassing of the catheter or acute pain and discomfort associated with urinary infection.

Removal of deposits by acidic solution (citric acid-magnesium oxide) has been shown to dissolve encrustation in vitro and is now used extensively in practice. Frequent irrigation could result in the damage of the mucus in the bladder.

A number of U.S. patents describe indwelling urinary catheter systems aimed at preventing urinary tract infection. These are mechanical devices with appropriate valve fittings to keep the drainage open while at the same time preventing ascending infection. U.S. Pat. Nos. 4,946,449 issued to Richard Davis and 4,878,901 issued to Hans Ernst Sachse are two typical examples. However, these do not have any prevention methods for encrustation. In general, mechanical systems are complicated and do not provide adequate protection from infection. U.S. Pat. No. 4,932,948 issued to Kernes et al., discloses the use of a funnel shaped insert at the end of the urinary catheter that serves as a reservoir to antimicrobial agents. The antimicrobial agent is simply mixed with the ethylene/vinyl acetate polymer during the fabrication of the funnel. The catheter surface itself does not carry any antimicrobial nor is it capable of preventing encrustation. U.S. Pat. No. 4,579,554 issued to Jacob Glassman discloses a design that provides for irrigation of the catheter tube. Frequent irrigation, however, could result in the damage of the mucus in the bladder.

U.S. Pat. No. 4,642,104 issued to Sakamoto et al. teaches the use of polymers carrying multicarboxyl, amino or sulfonic acid group capable of binding antibiotics through ion exchange. The ion exchange groups are chemically introduced into the molecules of the inside and outside wall of the urethral catheter by hydrolysis of certain functionalities that are present in the polymer that is coated on the surface of the catheter. Cationic antibiotics such as polymyxins or soap preparations such as benzalkonium chloride or benzethionium chloride, cyclohexidine or povidine-iodine remain on the surface due to the electrostatic binding. In order to introduce anionic groups on the surface of the catheter the surface has to be subjected to a series of chemical reactions and coatings, which could prove tedious and expensive.

U.S. Pat. No. 4,950,256 issued to Luther et al. teaches the use of an intravascular catheter comprising a cannula for insertion into a vascular system of a patient. This catheter is coated with a hydrophilic polyurethane-polyene composition for binding antithrombogenic materials and cationic polymyxin antibiotics. Luther et al., show that the absorption of the polymyxins into the hydrophilic polyurethane can be controlled by varying the initial concentrations, and the catheter is described as a time release intravascular catheter.

Amino phosphonates have been shown to prevent calcification of heart valves, and the process involves covalent bonding of the moieties to the biomaterial (C. L. Webb, et al., *Trans. Am. Soc. Artif. Intern. Organs*, XXXIV, 1851 [1988]). Silver alloys (R. J. McLean et al., *Can. J. Microbiol.*, 39 [1993]; Liedberg and T. Lundberg, *British Journal of Urology*, 65, 379–381 [1990]) have been reported to have been coated on urinary catheters and have been shown to be effective in preventing bacterial adherence.

The U.S. Pat. No. 5,295,979 teaches the use of two dissimilar metal coatings such as silver and platinum for creating an ionophoretic galvanic couple for driving silver ions in solution. This is achieved by sputtering a design of dots of the galvanic couple or by electroless plating of the successive metals.

Such coatings are hard to fabricate and require several manufacturing steps if multilayers are involved. The desired ratio of silver surface to volume for complete inhibition is about 25–50 square mm per mL of the growth medium. This is a difficult requirement to fulfill for a coating as the flow volumes are higher for urinary catheters.

The well publicized, ion-beam impregnated silver alloy catheters distributed by Spire Corporation do not provide protection in the lumen as the silver particles are embedded on the outside only. Also, these catheters do not protect against encrustation.

Recently, silver oxide coated Baxter catheters were clinically studied. The results showed that the catheters were not effective in preventing bacteriuria. Gram positive organisms were found to dominate (Riley et al., *The American Journal of Medicine*, 98, 349 [1995]).

Polyethylene oxide coatings have been found to be bacteriostatic and protein-resistant (D. K. Han, S. Y. Jeong, and Y. H. Kim, et al., *J. of Biomaterials Science, Polymer Edition*, 4(6), 579–89 (1993) and the references therein). Such coatings do not have any antibacterial properties and have temporary anti adhesive properties. Biofilms eventually form on such coatings.

U.S. Pat. No. 5,328,954 issued to Sarangapani and assigned to the assignee of present application discloses a coating for medical applications which is resistant to encrustation and bacteria. While this coating is very effective for short term use when used on some materials, it is not as effective for long term uses. The coating uses high area carbon filler which emparts a blackish grey color to the coating. As a result, for the sake of cosmetic appearance colorants could not be used, while coating on latex or other white polymer devices.

It is therefore a principal object of the present invention to provide a catheter for use in urological surgery for long indwelling situations or for managing urinary incontinence which inhibits the build up of bacterial biofilm and encrustation on the surface of the catheter.

Another object of the present invention is to provide a catheter for use in urological surgery or provide materials for devices used for managing urinary incontinence which causes a lower risk of infection than known catheters.

Another object of this invention is to create an antibacterial surface by blending the additives such as organic acids, Silver and/or Platinum with a dissolved polymer, Titanium dioxide filler, or a prepolymer polyurethane followed by drying the solvent or by a direct melt blending method with the plastic.

Yet another object of this invention is to provide a combination of acidifying chelating compounds that partition between the plastic and the body fluids such as urine, to provide an acidic pH on the surface.

SUMMARY OF THE INVENTION

There is a clear need to develop biopolymeric interfacial surfaces which minimize bacterial adhesion. The surface of the present invention which minimizes bacterial adhesion has been found to be particularly useful when used with urological devices. The urinary catheters including such a surface will a) prevent the adherence of bacteria, b) inhibit urease, and c) prevent calcium and magnesium phosphate deposits on the material. Such urinary catheters are especially useful when intended for use for extended periods. These advantages are achieved through surface modification of high surface area materials (filler) by means of a reactive hydrophilic polymer which forms a composite when painted on a braided nylon. The filler modified polymer paint can be coated on all plastic materials including latex. The coated catheter remains flexible and hydrophilic and allows equilibration of ions and offers a reactive surface.

Certain compounds may also be incorporated into medical grade plastics for providing a surface that is hydrophilic and antibacterial. Plastics such as C-Flex (sold by Consolidated Polymer technologies Inc, with the base polymer being Styrene/Butadiene), PVC etc. do not lend themselves to a permanent hydrophilic coatings. This invention overcomes the problem by the incorporation of certain compounds, that by virtue of their affinity for water, make the surface attract water molecules, while creating an acidic pH. The synergism with antibacterials such as silver achieves an effective bactericidal action. The low pH is conducive to the survival of Lactobacilli species, in the urinary tract that provide natural protection against other pathogens.

The present invention includes various polyurethane formulations that were coated on latex tubings and catheters. These formulations provide excellent adhesion to latex, and the chemical activity of the coatings inhibit bacterial adherence and encrustation. The present invention discloses methodologies of C-Flex materials modification by the same class of antibacterial additives, used for the polyurethane formulations.

A unique aspect of this invention is the combination of acidic chelating groups in combination with Silver and/or Platinum that gives rise to a continuous surface protection from bacterial biofilm formation. Such combinations are formulated as adhesive paints or as powders that can be melt blended in the plastic.

The present invention differs from the prior art in several ways: 1) it uses the adhesive nature of —NCO groups as well as its reactivity to couple various antibacterials; 2) it uses phosphonate and or carboxylate moieties as calcium solubilizing agents, 3) it uses 1 micron or lower level high area metallic silver as an antibacterial mixed with high area materials such as Titanium dioxide or silverized carbon; 4) it uses antibacterials that could covalently bind to the —NCO group of a prepolymer such that the antibacterial would become a part of a hydrophilic polyurethane backbone of the coating, 5) it uses aminopolycarboxylic acids, Citric acid and other similar carboxylic acids, aminophosphonic and aminosulfonic acids; 6) it uses noble metal blacks such as Pt black along with silver powder to enable the continuous slow release of $Ag^+$ ions; 7) it uses Fillers such as $TiO_2$ to bind the polyphosphonic acid by chemisorption. In addition, the presence of Polyox, (Union Carbide) a high molecular weight polyethylene oxide, makes the surface bacteriostatic and slippery.

The current invention overcomes the problem encountered in connection with the use of two dissimilar metal coatings in two ways. By using a high area platinum black and high area silver powder dispersed on a $TiO_2$ containing paint formulation that is hydrophilic, the desired surface area/volume ratio is achieved. The real surface area per unit area of the coating is much higher than the geometric area of a simple metallized coating on hydrophobic plastics. Thus, the bacterial inhibition is achieved not only by the released silver ions but also by the hydrophilicity and acidity.

The acidity is provided by the presence of phosphonic acids and carboxylic acids shown in various examples. The usefulness of silver ions as antibacterials is limited by the solubility product constant of AgC1 ($10^{-13}$). The body fluids such as urine contain a high concentration of sodium chloride that immediately converts the free silver ions into silver chloride. The concentration provided by this silver's antibacterial properties depends upon the ratio of the rate of silver ions generated to the rate of growth of bacteria. In this invention the presence of complexing acids of chelating type (DPTA, Diamino propanol Tetracetic acid) Citrate, polyphosphonate complexes of silver are much more soluble than silver chloride (the solubility product values are of the order of $10^{-8}$) and exist in equilibrium with silver chloride give a remarkable effect of a) providing a steady concentration of soluble silver at bactericidal concentration b) providing acidic pHs necessary to inhibit most pathogens and c) providing a surface that prevents the nucleation of encrusting calcium phosphate.

The providing of a more soluble form of silver compounds on the surface (silver citrate, silver DPTA, etc.) instead of silver ions that are immediately converted to silver chloride on the surfaces make this invention unique. The additional of a very small amount of Platinum, as illustrated in the examples enhances the activity of the combination of silver and chelating acids.

The formulation of the present invention makes it significantly more useful and effective than the formulation described in U.S. Pat. No. 5,322,520 which claims an ionotophoretic structure of two layers of dissimilar metals such as silver and platinum or copper in a plastic matrix separated by a conductive plastic layer. The current invention not only overcomes the difficulties associated with fabrication of separate layers from this prior art by providing means to achieve a one pot formulation but also demonstrates the efficacy of silver in the presence of acidic components with and without platinum.

These and other features and objects of the present invention will be more fully understood in the following detailed description, which should be read in light of the accompanying drawings.

DETAILED DESCRIPTION OF THE PREFERRED EMBODIMENTS

Figure 1A:
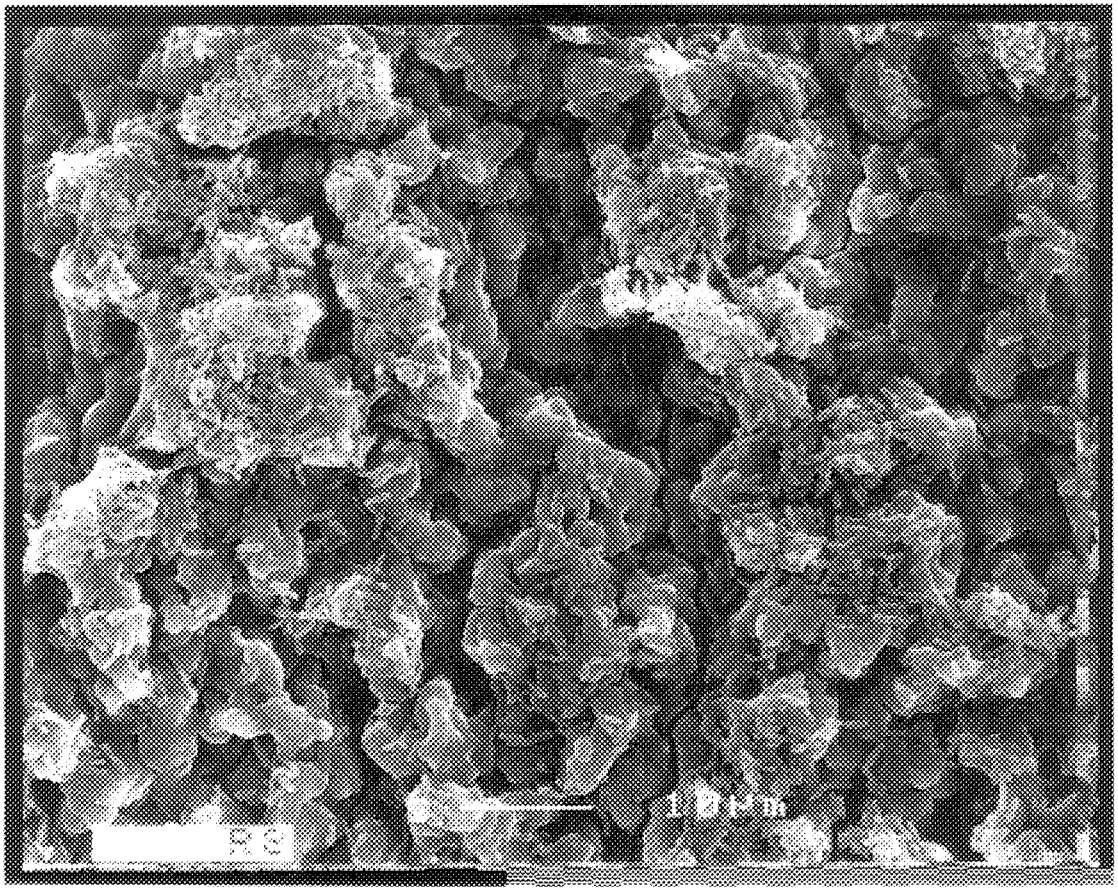
FIGS. 1a and 1b are graphs that shows the morphology of the uncoated and coated latex surfaces.
Figure 1B:
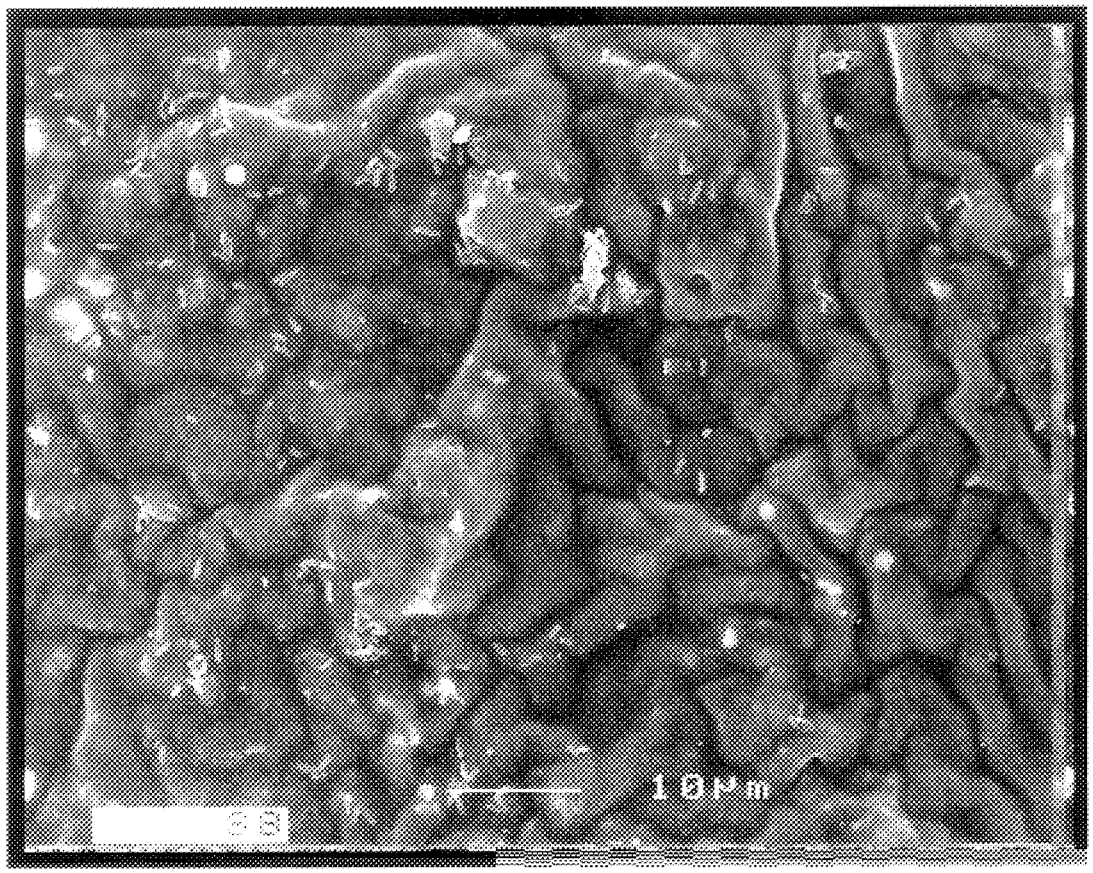
Figure 2A:
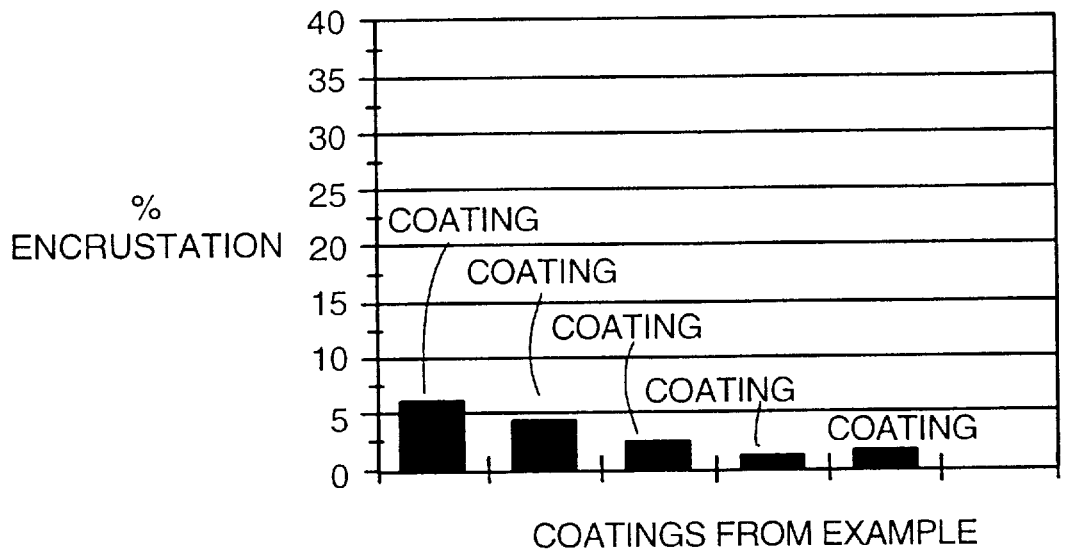
FIG. 2a. is a graph that shows bacterial encrustation data for controls and samples from Examples of the present invention.
Figure 2B:
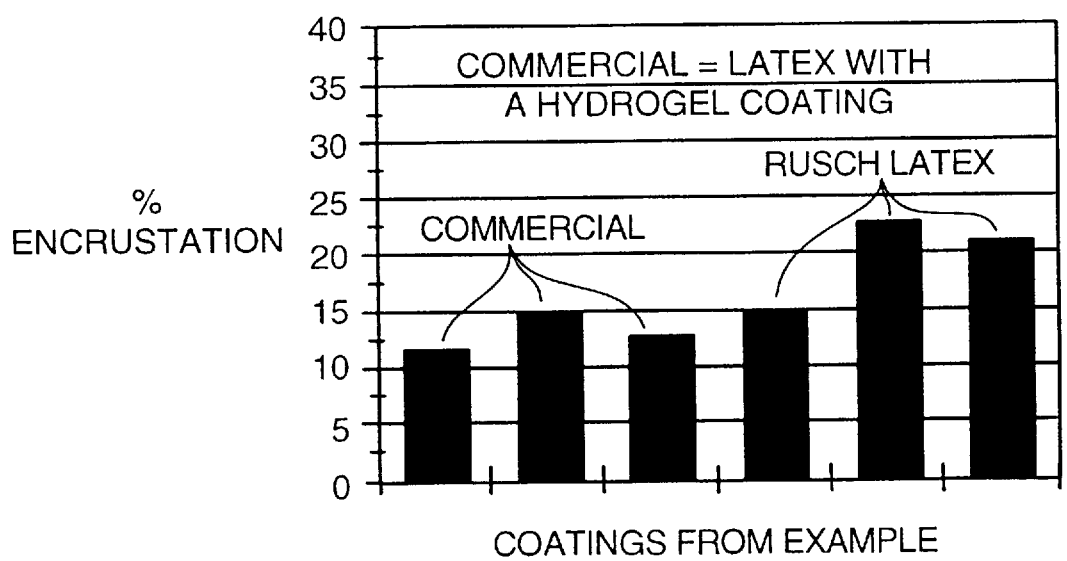
FIG. 2b. is a graph that shows bacterial encrustation data for latex and commercial hydrogel coated latex.

The coating for catheters of the present invention that minimizes encrustation and/or infection, as encountered in known urinary catheters includes a coating having a hydrophilic polyurethane pre-polymer, a high area filler which is preferably carbon or Titanium dioxide (but silica, alumina and other filling agents may be used), anti-bacterial agents such as quinolones and urease inhibiting agents such as silver ions and EDTA. The current invention overcomes the fabrication problems of multilayer metallic coatings in two ways. First, by using a mixture of high area platinum black and high area silver powder dispersed on a $TiO_2$ containing paint formulation that is hydrophilic, a favorable surface area/volume ratio is achieved. The real surface area per unit area of the coating is much higher than the geometric area of a simple metallized coating on hydrophobic plastics. Thus, the bacterial inhibition is achieved not only by the released silver ions but also by the hydrophilicity and acidity.

The acidity provided by the presence of phosphonic acids and carboxylic acids shown in various examples presented below is an another added advantage. The usefulness of silver ions as antibacterials is limited by the solubility product constant of AgCl, due to the presence of complexing acids of chelating type that shift the equilibrium to give a remarkable effect of a) providing a steady concentration of soluble silver at bactericidal concentration and b) providing acidic pHs necessary to inhibit most pathogens.

By providing a surface that kills harmful bacteria, devices such as catheters or self-administered urethral plugs, have a much lower probability of carrying line pathogenic bacteria to the bladder, thus lowering the incidence of UTI by an enormous extent. Plastics such as PVC or synthetic rubber, such as styrene-butadiene or even silicone, are hydrophobic by nature.

Plastics such as C-flex, silicone, PVC, etc. do not lend themselves to a permanent hydrophilic coating and this invention overcomes that problem by incorporation of certain hydrophilic compounds or polymers in the plastic resin. In addition, this invention discloses synergic effects of antibacterials that achieve an effective kill of harmful gram negative species such as *E. coli.* The hydrophilic compounds not only make the surface attract water molecules but also render a low pH of 4–5, on the surface that discourages bacterial growth. Such a low pH is naturally caused by Lactobacillus species that thrive in the urethra of healthy females. There are several reports on the ability of low pH to deter pathogenic bacteria.

In addition, certain combinations of the above hydrophilic compounds with antibacterials, such as silver, resorcinol monoacetate, EDTA, DPTA and carboxylic acids give surprising effects described below. The ability of some of the formulations to kill *E.coli* on contact and allow Lactobacilli to survive is demonsrated in some examples.

In another embodiment of the present invention, hydrophilicity and antibacterial activity is incorporated in hydrophobic rubbers used in the medical industry such as Styrene - Butadiene derived rubbers and Poly vinyl chloride. Applications requiring antibacterial surfaces, such as catheters of all kinds, stents, urethral plugs, and synthetic biomaterials can use the formulations described herein as a coating or as part of the device itself.

The infection and colonization in urinary catheters mostly occur in the inner lumen of the catheters. The highly adherent coatings described in this application, when used inside the lumen surface, discourage bacterial adherence.

The fact that the coatings described in this invention are:

a) resistant to bacterial colonization for up to seven days, b) resistant to encrustation for up to seven days as confirmed by accelerated bacterial perfusion studies, and c) are very smooth and slippery when wet with excellent adhesion to latex and other medical polymers make these ideal for long indwelling urinary catheter applications.

Aminopolycarboxylic acids such as ethylene diamine tetraacetic acid, and iminodiacetic acid are powerful chelating agents for Ca and Mg at pH's between 8–10. At pH=7, (the normal urine pH), ethylene diamine tetraacetic acid exists mostly in the form of $H_2 Y^{2-}$ ($Y^{4-}$ is the tetra ion) and small amounts of $Y^{4-}$, $H_3 Y$— and $H_4 Y$. At pH 10, the concentration of $Y^{4-}$ is 40% of the total concentration of the ethylene diamine tetraacetic acid. In a situation where $H_2 Y^{2-}$ is present on the biomaterial in reasonably high concentration, the increase in pH due to urease action will be somewhat controlled due to the release of the acidic protons and any further increase would result in the formation of $Y^{4-}$ which will engulf $Ca^{2+}$ and $Mg^{2+}$ at pH values between 8 and 10 and prevent the nucleation of hydroxyapatite and struvite on the catheter surface. When the pH of the urine becomes 7, the bound calcium and magnesium are released by ethylene diamine tetraacetic acid. It must also be noted that when the pH of the urine approaches 5 or below, ethylene diamine tetraacetic acid can act as powerful urease inhibitor and also possesses antibacterial properties by chelating $Ca^{2+}$ from the cell wall. Therefore the advantages of using ethylene diamine tetraacetic acid and related ligands at both high and slightly below neutral pH are highly beneficial in achieving the goals described above. Aminophosphonates, polyvinyl phosphonates and diphosphonates have been used as calcium deposit inhibitors in the formulations described in this invention.

Among the antibacterial agents the quinolones are currently undergoing more innovation, and the interest far exceeds that in the cefalosporins and aminoglycosides. The quinolones are bactericidal and the minimum inhibitory concentration, in general, increases in presence of divalent cations due to their tendency to form complexes. The use of resorcinol or resorcinol monoacetate antiseptic agent has already been established for external uses. Incorporation of resorcinol monoacetate in collagen based biomaterials show dramatic evidence of bacterial inhibition even at a 2% w/w concentration. When this functionality is bonded to the catheter surface, one might expect to see long-term antibacterial effects.

In order to enrich the surface by the organic functionalities, a polymer was used. Extensive search of different commercially available polymers revealed the availability of a hydrophilic polyurethane prepolymer sold by W.R. Grace under the trade name Hypol.

Hypol 5000 (a pale yellow, high viscosity liquid) which is a MDI (methylene diisocyanate) based prepolymer that contains 2.55 meq/g of free —NCO group and its various reactions with —OH and —COOH groups are shown below.

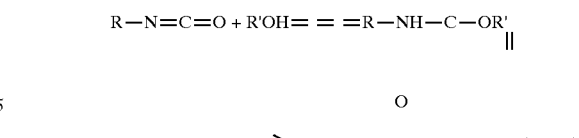

$$R-NCO + R'-COOH \longrightarrow R-NH-CO-R' + CO_2 \quad (amide)$$

The highly reactive —NCO groups were reacted with ethylene diamine tetraacetic acid, iminodiacetic acid, resorcinol monoacetate, and quinolones. While several reaction sequences with different rate constants are possible during the coupling and curing processes, IR spectral data indicates the absence of —NCO groups and the presence of urethane, —COOH and —OH groups in the cured sample. Polyethyleneimine that shows antibacterial properties has been successfully incorporated in the formulations described in the present invention.

High area carbon can be used as an excellent support material for polymers such as Hypol. Diluted Hypol after chemical coupling with the appropriate compound blends very well with hydrophilic Cabot M-1300 carbon and forms a paint-like formulation. The surface area measurements of carbon loaded with Hypol tubings after complete cure showed an area of 3000 $cm^2$/g. The surface area of a silicone tube used as control in the experiments was only 270 $cm^2$/g. Thus the use of high area carbon in the formulation allows surface concentrations of the chelating and anti-bacterial agents to be at least one order of magnitude higher than what would be possible without the carbon. Hypol also proved to be an excellent binder for carbon and during all incubation studies of the various Hypol/Carbon catheter materials, microscopic carbon particles were not detected.

Substitution of titanium dioxide for carbon in such coatings yielded coatings that were excellent in texture, color and performance. A filler such as $TiO_2$ was formulated with polyphosphonic acid, silver powder and platinum black. (5–10%, 3–5% and 0.05–0.2% respectively). This powder was then reactively mixed with Hypol to make paint-like formulations. The addition of 0.05–0.2% platinum black to the formulation containing silver enhances the activity of silver and the cure rate of the coatings. The formulations are coatable directly on clean polyurethane surfaces. Latex surfaces may be successfully primed with diisocyanatohexane (5% in toluene) in the presence of tin octoate. After drying in vacuum oven for one hour at 60° C. (to remove the toluene), the tubes should then be coated with Hypol 2002 (10% in acetone). The coated tubes are then cured overnight.

The urease concentration on the surface will be of micromole quantities. The aminopolycarboxylic ligands are capable of reversibly binding $Ca^{2+}$ or $Mg^{2+}$ depending upon the pH. Also the high surface concentrations of powerful urease inhibitors, such as $Ag^+$ along with antibacterials provide a powerful barrier against infecting bacteria and urease. The equilibration between the surface and the urine must be rapid due to the expansion of the hydrogel or ionomer coatings allowing diffusion of various species.

EXAMPLE 1

This example describes groups of formulations (Table I) that were successfully coated on latex tubings. The efficacy of the coatings toward bacterial encrustation were evaluated.

A typical procedure involved weighing a known amount of Hypol™, one or more active ingredients such as DPTA, citric acid, Benzoic acid nitroxolin, resorcinol monoacetate, phosphoserine, phosphorylethanolamine, norfloxacin, ciprofloxacin, etc. (All these chemicals were obtained from Fluka, Sigma-Aldrich chemical companies.) and mixing under warm conditions using a stirrer bar. The mixture was diluted with acetone and THF followed by the addition of the filler. The viscosity was adjusted by adding Polyox™ in methylene chloride. Thoroughly washed and dried latex tubings from Rusch Co. were used as substrates. Typically, the formulation was allowed to flow on the inner surface of the tubes using a vacuum line, and the outer surface was coated by simple dipping. Curing over 2 days at room temperature resulted in adherent, shiny coatings that did not crack or peel on stretching the coated tube up to 5 times its original length. Incubation at 37° C. in PBS for 3 weeks did not affect the quality of the coating.

FIGS. 1a, 1b, 2a and 2b, respectively, show the morphology of the coated vs. uncoated tubes and encrustation data on some of these coatings. All samples were autoclaved before the tests.

All the bacterial encrustation experiments were carried out in an "invitro" improved reactor model published by the inventor.(S. Sarangapani et al. J. Biomedical Mat.Res.29, 1185–1191, 1995.) The encrustation model results show the effect of phosphoserine, phosphorylethanolamine, and polyphosphonate formulations in preventing calcium deposit by about 50% to less than 1% compared to the control.

TABLE I

DETAILS OF COATING FORMULATIONS.

| Identification Active Ingredients | Group | Base Polymer | Polyox* | Silver | Filler |
|---|---|---|---|---|---|
| DPTA, RMA, Phosphoserine, Polyvinylphosphonic Acid,Hydroxyethyl idene di phosphonic acid,(HEDP) Nitrofurantoin, Phosphorylamine, Fluoroquinolones, Organic Carboxylic Acids eg. citric acid | I | Hypol ™ 2002 | Polyox MW, 100,000 | Silver Citrate | Carbon black or TiO$_2$ |
| DPTA, RMA, Phosphoserine, Polyvinylphosphonic Acid, Nitrofurantoin, Phosphorylamine, Fluoroquinolones, Organic Carboxylic Acids eg. citric acid | II | Hypol ™ 2002 | Polyox MW, 100,000 | Silver Powder 1 micron | Carbon black or TiO$_2$ |
| DPTA, RMA, Phosphoserine, Polyvinylphosphonic Acid,HEDP Nitrofurantoin, Phosphorylamine, Fluoroquinolones, Organic Carboxylic Acids eg. citric acid | III | Hypol ™ 2002 | Polyox MW, 100,000 | Ag Powder Pt black | Carbon black or TiO$_2$ |

*The Polyox can be coated as a final overcoat or included in the formulation.

EXAMPLE 2

A formulation where polyvinyl phosphonic acid or hydroxy ethyl diphosphonate (HEDP) was mixed directly with the Hypol prepolymer is described in this example. The general formulation was as follows:

| | |
|---|---|
| Polyvinyl Phosphonic acid = or Hydroxy ethyl bisphosphonate | 0.2–1.0 g |
| Silver Powder = | 0.5–1.0 g |
| Silver citrate = | 0–0.2 g |
| M-1300 carbon or Degussa = titanium oxide | 0.1–0.5 g |
| Hypol 2002 = | 10–15 g |
| RMA = | 0.2–0.5 g |

The first four ingredients are ground well and mixed with Hypol 2002 under warm conditions on a hot plate. Then acetone ~15–20 mL is added, mixed, sonicated after the addition of resorcinol monoacetate. The coating formulations of Group II in Table I are variations of the formulation described in this example.

EXAMPLE 3

This example describes formulations that substitute carbon with pigment such as titanium dioxide. It was also identified that the addition of platinum black (30 m$^2$/g surface area) (Johnson Matthey) to silver powder (average particle size 1 micron) (Alfa or Cerac) in the following formulations enhances the effect of the surface to resist bacteria for longer periods of time.

| | A | B |
|---|---|---|
| Polyvinyl phosphonic acid = | 1.0 g | 1.0 g |
| Ag powder = | 1.0 g | 1.0 g |
| Pt black = | 0.2 g | — |
| TiO$_2$ (Degussa, P25) = | 0.3 g | 0.3 g |
| Hypol 2002 = | 11 g | 11 g |
| Resorcinol monoacetate = | 0.5 g | 0.5 g |
| Copper phthalocyanine dye = | 0.05 g | 0.05 g |

The above blend is mixed well after grinding the solid ingredients in a mortar and pestle, added with 20 ml acetone containing Hypol, sonicated, and coated on latex or polyurethane surfaces. The coatings cured within 48 hr. at ambient temperature. The addition of platinum accelerates the cure rate within the bulk of the coating. They can also be cast as films.

Light grey colored coatings with excellent gloss and smoothness were obtained. The addition of 0.05 g of copper phthalocyanine (coloring pigment) resulted in a bluish grey coating.

EXAMPLE 4

This example describes the results on long-term biofilm experiments conducted under a high concentration of continuous bacterial challenge.

Test Materials: Catheter materials (latex control, coating from Example 3A and 3B) were tested. In addition silicon rubber, another commonly used catheter material (obtained from Dapro, Tulsa Okla.) was also used for comparison. Prior to use, discs were cut out of these catheters and used for biofilm testing as described below.

Biofilm Experiments: Biofilm experiments were conducted using a Robbins Device (Nickel, J. C., I. Ruseska, J. B. Wright, and J. W. Costerton. "Tobramycin resistance of *Pseudomonas aeruginosa* cells growing as a biofilm on urinary catheter material." *Antimicrob. Agents Chemother.* 27:619–624. 1985). About 7 mm diameter discs were cut from the collar of the catheters using a cork borer. 8–10 discs were obtained of each material for testing. Mounting these materials into the Robbins device was accomplished by placing melted paraffin wax into the Robbins device plug and laying the disc over it. With some plugs, it was necessary to cover the edges of the plug with some paraffin. These materials were not sterilized prior to use. This allowed us to test their ability to resist colonization by P. aeruginosa as well as any other organisms which may have arisen by contamination. Our rationale here was that colonization of catheters by any organism may eventually present a clinical problem.

Discs were mounted into the Robbins device as follows: Silicon rubber (ports 1 and 2), latex rubber control (ports 3–9), (ports 10–17), (ports 18–25) [numbering in the direction of flow, i.e., 1 at inlet, 25 at outlet]. The flow was set at 60 mL/h.

Prior to inoculation of the culture, the Robbins device was flushed with sterile $H_2O$ for several hours. This was done to ascertain whether any disks would become dislodged. Although several discs needed to be remounted during this trial phase, all discs remained intact once the culture was inoculated.

Following incubation, the discs were aseptically removed from the culture and vortexed briefly for 2 sec in sterile deionized water to remove the unattached organisms. Biofilm organisms were dislodged by placing the organisms in 10 mL sterile water and sonicating for 10 min in a bath sonicator. Serial dilutions of the dislodged organisms were performed with sterile phosphate buffered saline (McLean, R. J. C., J. Downey, L. Clapham, and J. C. Nickel. "A simple technique for studying struvite crystal growth in vitro." Urol. Res. 18:39–43. 1990.), and the organisms were then plated onto nutrient agar plates (Difco) and incubated overnight at 37° C. After colony counting, results were reported as colony forming units per disc (CFU/disc).

Analysis of Data: Data analysis of $\log_{10}$ (CFU/disc) values was performed by one way ANOVA using SigmaStat software (version 1.01, Jandel Scientific, San Rafael, Calif.). The results were also plotted graphically using SigmaPlot software (version 5.0, Jandel). Logarithmic transforms of the data, i.e., comparisons of log (CFU/disc) values as opposed to CFU/disc values, was done to ensure normal distribution of data.

Figure 3A:
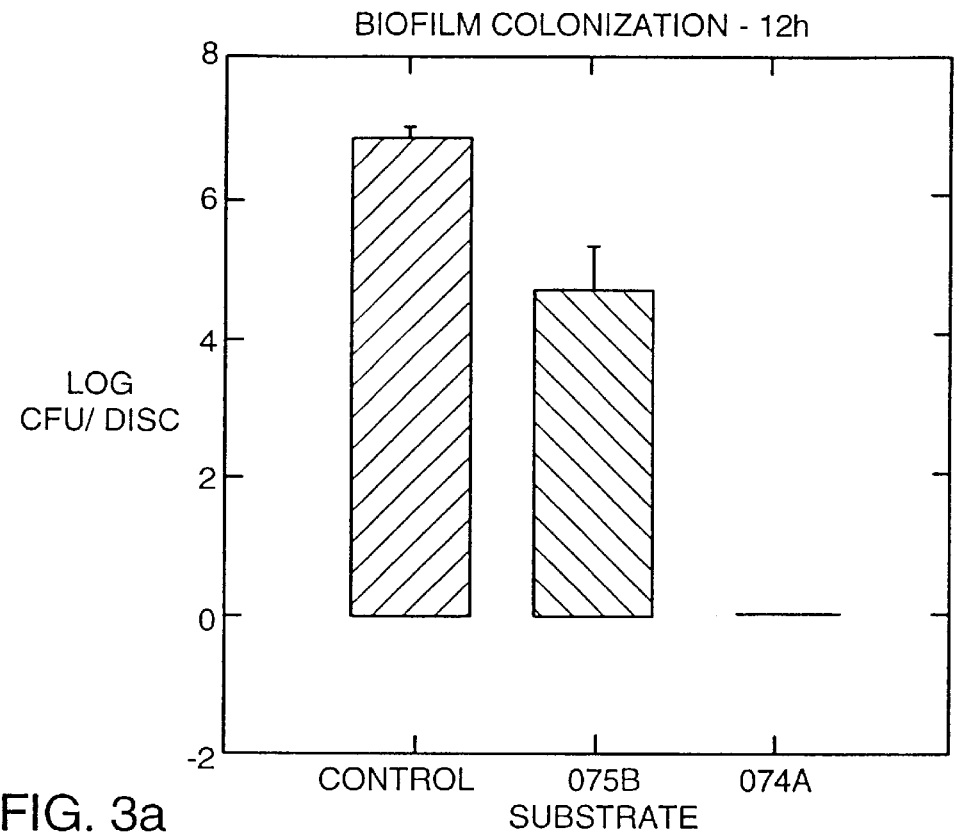
FIGS. 3a and 3b are graphs that show the extent of biofilm formation (12 h and 24 h) on the coated samples from Example 3 vesus the control.
Figure 3B:
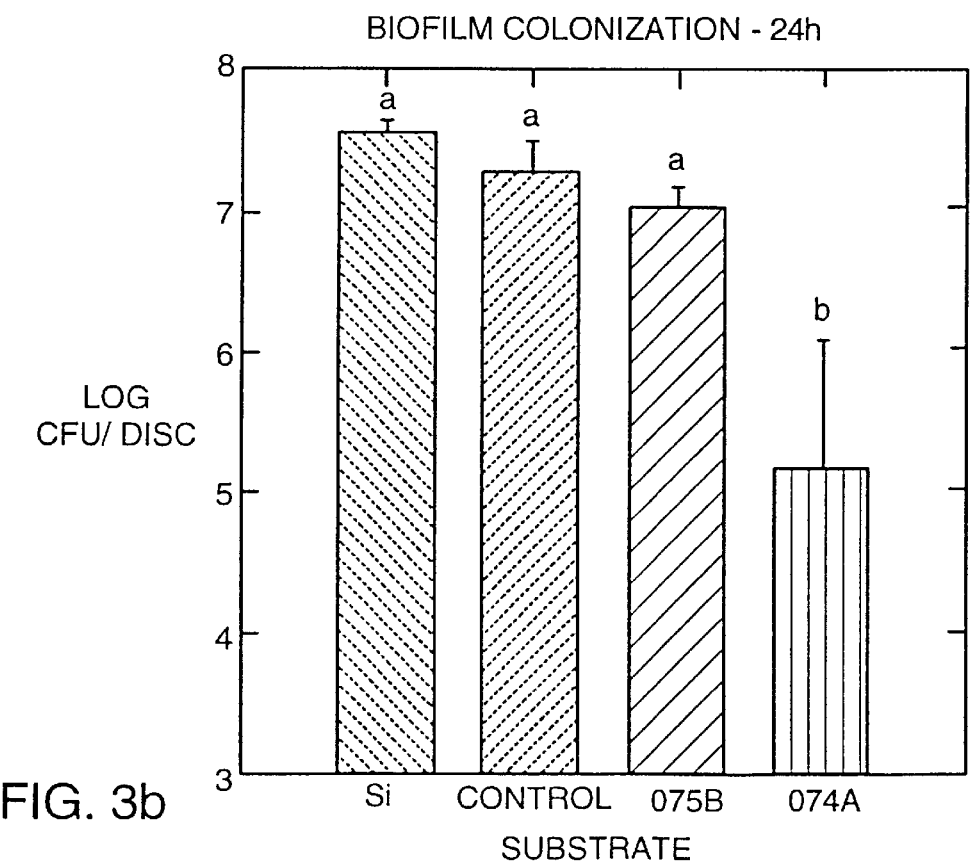
Figure 4A:
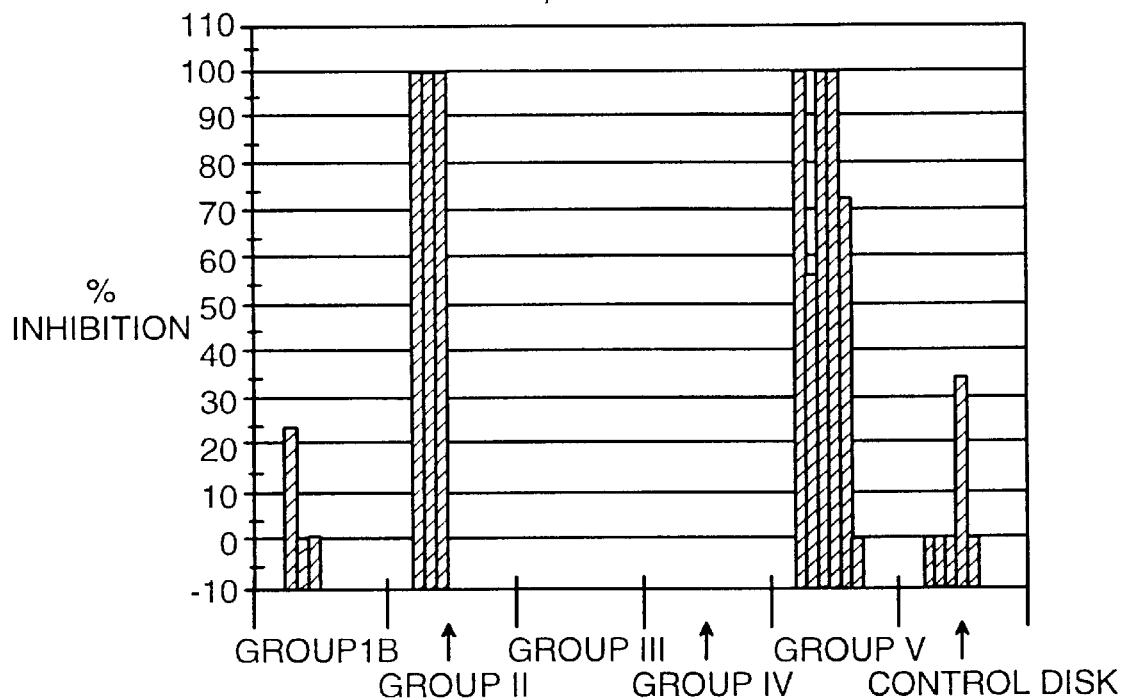
FIGS. 4a, 4b, 4c, and 4d are graphs showing the inhibition efficiencies of C-flex materials incorporated with combined additives used in the present invention.
Figure 4B:
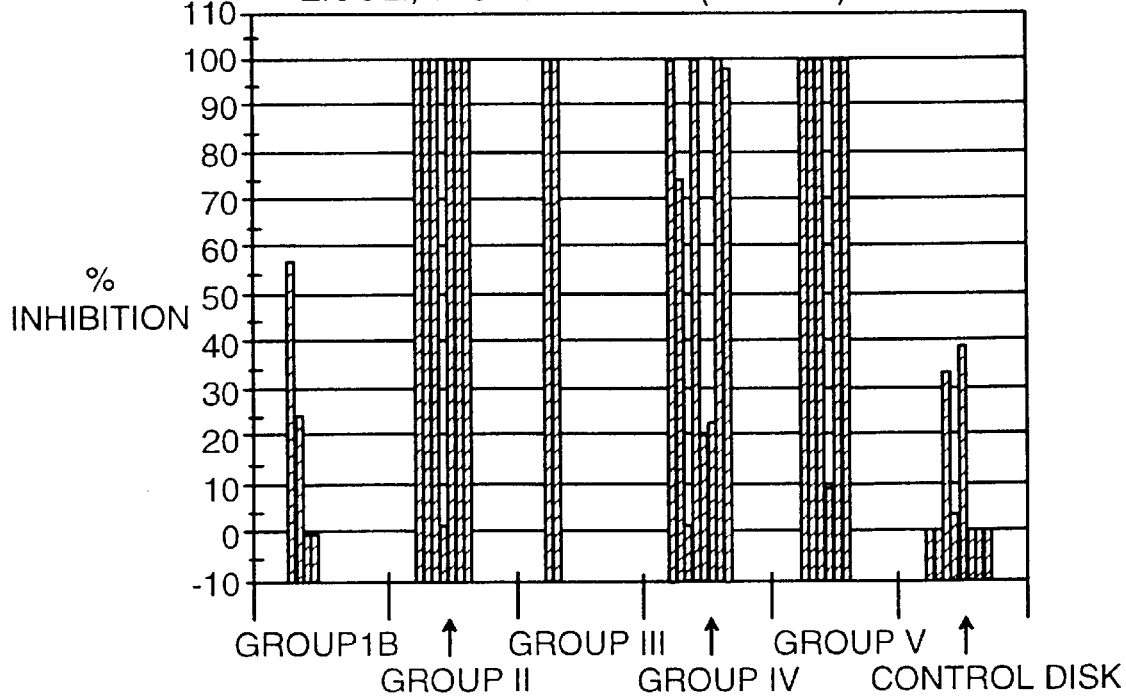
Figure 4C:
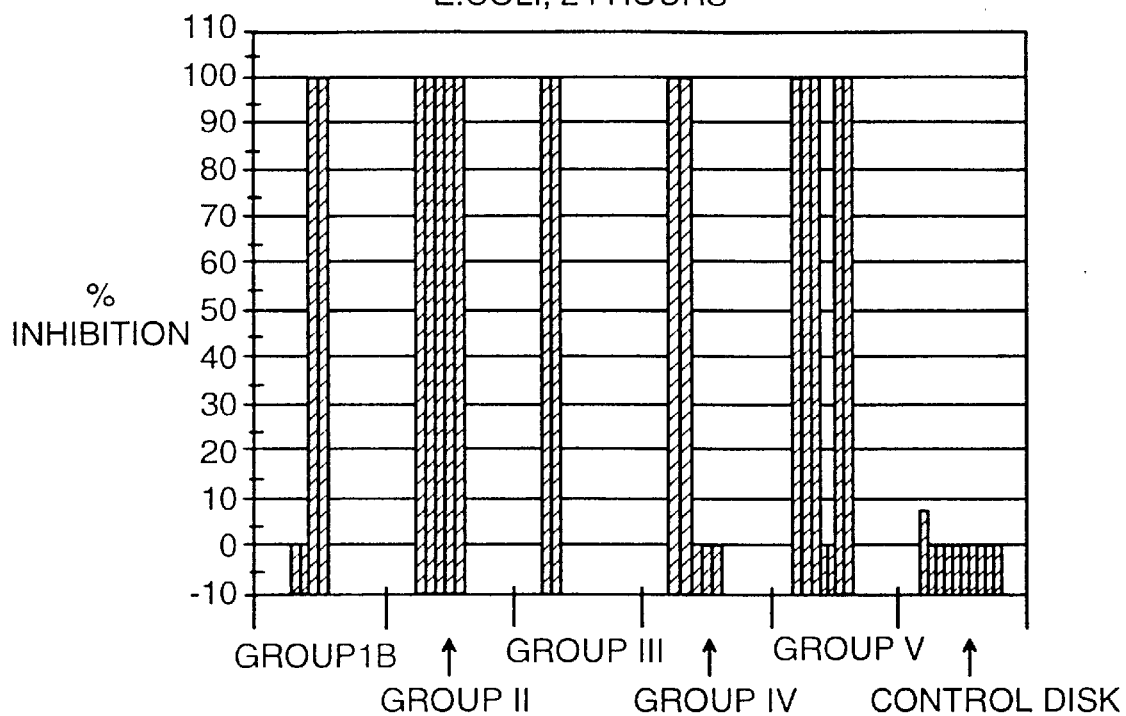
Figure 4D:
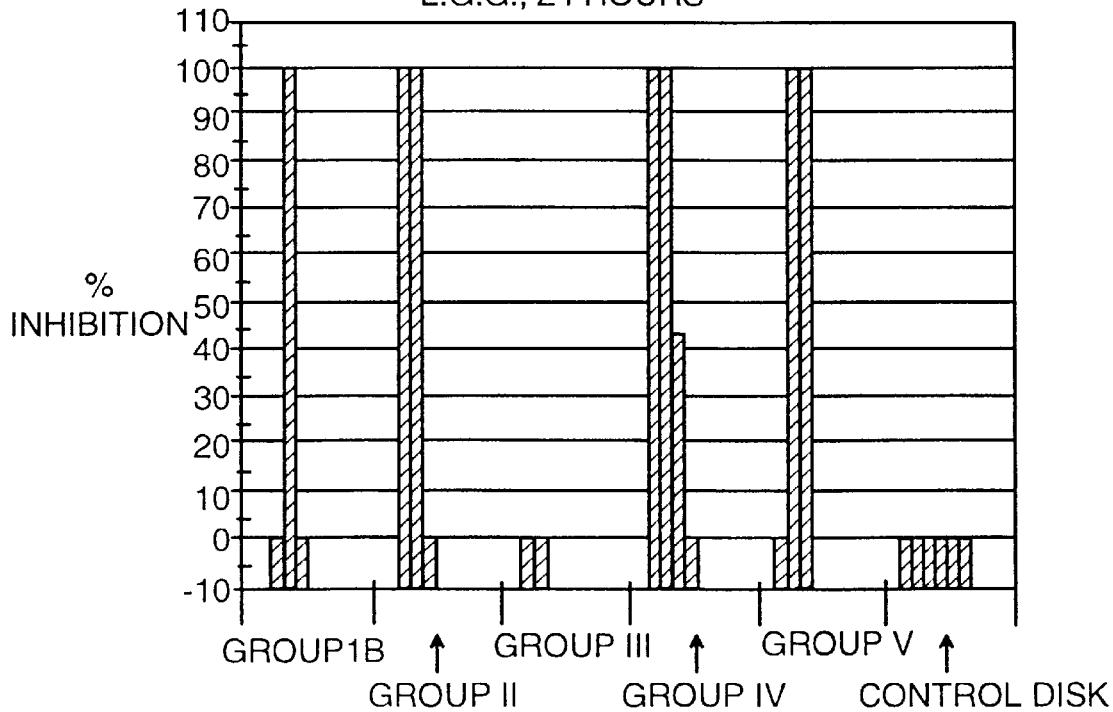

P. aeruginosa readily colonized all test surfaces used in this experiment. Graphical presentation and statistical analysis of the data is given in FIG. 3a (12 h colonization) and FIG. 3b (24 h colonization). Significant reduction in adherent P. aeruginosa was noted between the coating from Example 3A and all other materials at both 12 and 24 h. These differences exceeded 3 orders of magnitude.

EXAMPLE 5

This example describes the biocompatibility of selected coatings from example 3A in rabbits.
USP MUSCLE IMPLANTATION TEST IN RABBITS WITH HISTOPATHOLOGY. (Carried out by NaMSa, Ohio)

Test Article: Coated tubings, on Tecoflex Polyuerethane-approximately 7 French, size coating from example 3A Preparation: The test article was cut and trimmed to 1 mm×10 mm. Sterilized by EO.

Procedure: Two healthy adults New Zealand White rabbits weighing at 2.5 kg were used as test animals. The back of each animal was clipped of fur on both sides of the spinal column. Loose hair was removed by alcohol wipe after clipping and the paravertebral muscles were anesthetized. Strips of sterile test article were implanted into the right paravertebral muscle of each rabbit; strips of USP control plastic were implanted in the left paravertebral muscle of each rabbit.

The animals were euthanatized 5 days after implantation and the entire paravertebral muscle on each side of the vertebrae was removed. Tissues were fixed in 10% neutral buffered formalin. After fixation, cross sections of the muscles were made to locate the implants. The tissue surrounding the implant was examined macroscopically. The implant sites were histologically processed and stained with hematoxylin and eosin for microscopic examination by a board certified pathologist.

TABLE II

Results of Macroscopic Examination:

| Rabbit No. | Test Coating from Example 22b | Control |
|---|---|---|
| 87154* | 0 | 0 |
|  | 0 | 0 |
|  | 0 |  |
|  | 0 |  |
| 87111* | 0 | 0 |
|  | 0 | 0 |
|  | 0 |  |
|  | 0 |  |
| Average: | 0.0 | 0.0 |
| Average (test)—Average (control) = 0.0 |  |  |

| Score | Encapsulation |
|---|---|
|  | Scoring Key |
| 0 | No capsule or adverse reaction (other than minimal hemorrhage) |
| 1 | Up to 0.5 mm capsule or reaction area |
|  | 0.6 to 1.0 mm capsule or reaction area |
| 3 | 1.1 to 2.0 mm capsule or reaction area |
| 4 | >2.0 mm capsule or reaction area |
|  | Reaction Index |
| 0–0.5 | Not significant |
| 0.6–1.0 | Trace |
| 1.1–2.0 | Slight |
| 2.1–3.0 | Moderate |
| ≧3.1 | Marked |

Macroscopic: The reaction was not significant as compared to the USP negative control implant material.
Microscopic: The reaction was a nonirritant as compared to the USP negative control implant material (see attached report).
Comments: *Previous use history traceable in laboratory records.

EXAMPLE 6

This example illustrates the efficacy of coatings from example toward the adherence of Proteus Mirabalis HI4320, (isolated from a pylonephritic patient, Baltimore VA Hospital) in human urine (filter sterilized), as compared to an uncoated and a commercial antibacterial catheter.

PROCEDURE

A lid with the catheter segments attached to the wire hooks (which was described in U.S. Pat. No. 5,328,954, the teachings of which are incorporated herein) was placed on a jar containing sterile phosphate buffered saline (PBS). The catheter segments were allowed to equilibrate in PBS for 1 hour at 37° C. The lid was then transferred to a jar containing approximately 250 ml of the reaction medium such that approximately one half of the catheter segment length was immersed in the reaction medium. Care was taken to avoid contact of the wire hooks with the reaction medium. The lid for each reaction container was fitted with segments from only one catheter type. The lid for a single reaction container was fitted with up to 12 catheter segments each individually attached to a single wire hook. The reaction medium was inoculated with approximately $2 \times 10^4$ cfu/mL $P.$ $mirabilis$ IE4320 and Cfa/mL incubated for 3 h at 37° C. while stirring. After a 3 hour incubation the lid with attached catheter segments was removed from the reaction container and placed on a jar containing approximately 250 sterile PBS. The catheter segments were washed by immersion in three consecutive jars of sterile PBS and then placed into fresh sterile human urine for 24 hour incubation. Some catheter segments were removed for subsequent assessment of the attachment of $P.$ $mirabilis$ to the catheter surface. The lid with the remaining catheter segments attached was placed on a fresh reaction container with fresh sterile reaction medium and the apparatus was incubated for an additional 24 hours, the washing and reincubation procedure was repeated until a portion of the catheter segments had incubated in the reaction medium for a total of 96 hours. At the end of each 24 hour incubation, the number of $P.$ $mirabilis$ cells in the reaction medium was quantitated and results were expressed as cfu\mL of reaction medium.

Microbiological Assessment—Quantitative counts from the reaction medium in which the catheter segments were immnersed, Uncoated controls
- 24 hr—$1.3 \times 10^8$ cfu\mL
- 48 hr—$7$–$6 \times 10^5$ cfu\mL
- 72 hr—$1$–$2 \times 10^6$ cfu\mL
- 96 hr—$2,7 \times 10^6$ cfu\mL Coated tubes from this invention.(Example 3 coating A).
- 24 hr—no growth
- 48 hr—no growth
- 72 hr—no growth
- 96 hr—no growth BardexI.C. Foley Catheter (Silver Coated)
- 24 hr—$1.7 \times 10^6$ cfulml
- 48 hr—$3.9 \times 10^5$ cfu\mL
- 72 hr—$6.9 \times 10^5$ cfu\inL
- 96 hr—$1.2 \times 10^6$ cfu\mL

EXAMPLE 7

This example demonstrates the use of active ingredients such as phosphonic and carboxylic acids with or without silver or platinum.

The C-flex resin RTO-050 from CPT Inc. was used for this Example. Typically, 10% clear solutions of the resin were prepared by dissolving the resin in a solvent (to 50 g of C-flex resin added 300 g of Toluene and 150 g of Decalin, and refluxed using a water condenser while stirring the mixture vigorously). Typically, to a given volume of the polymer solution the additives were added, ultrasonicated, and cast on glass petri dishes. After the complete evaporation of the solvent, followed by vacuum drying, the cast discs were baked in a furnace at 250° C. for 7 minutes to mimic the molding conditions.

The following table shows the various additives that were combined with dissolved C-Flex.

TABLE III -A

Group IB—1% citric acid+0.5% silver
Group II—2% citric acid+0.5% silver
Group III—1% citric acid+0.5% silver+0.5% butyl paraben
Group IV—1% hydroxyethylidene phosphonic acid+0.5% silver
Group V—1% hydroxyethylidene phosphonic acid+0.5% silver+0.025% platinum The percentages are w/v.

The resulting discs were gamma sterilized including the controls without any additives, but treated as described above. The pH effects of two 1 cm discs when incubated in 20 mL of synthetic urineeee at 37° C. are shown below.

TABLE III-B

C-Flex pH Tests in Synthetic Urine* pH 5–8.

| | | pH Measurements (incubation at 37° C.) | | | | |
|---|---|---|---|---|---|---|
| | Description | T = 0 min | T = 5 min | T = 15 min | T = 45 min | T = 60 min |
| 042-120B (Baked)** | HEDP/CFLEX | 5.75 | 4.64 | 4.34 | 4.17 | 4.14 |
| 042-120B (Unbaked) | HEDP/CFLEX | 5.75 | 5.14 | 4.99 | 4.73 | 4.70 |
| 042-109D | Aspartic Acid/CFLEX | 5.75 | 5.69 | 5.69 | 5.38 | 5.33 |
| 042-100C | PVP/CFLEX | 5.75 | 5.68 | 5.69 | 5.68 | 5.69 |
| 042-141A | Citric Acid/CFLEX (Baked)** | 5.69 | 3.68 | 3.67 | 3.64 | 3.64 |
| 042-141B | Citric Acid/CFLEX (Unbaked) | 5.69 | 4.39 | 3.64 | 3.42 | 3.41 |
| 042-141C | HEDP/Pt/Ag/CFLEX** (Baked) | 5.69 | 2.99 | 2.82 | 2.78 | 2.79 |
| 042-141D | HEDP/Pt/Ag/CFLEX (Unbaked) | 5.69 | 4.83 | 4.73 | 4.64 | 4.65 |
| 046-035A (Baked)** | HEDP/Steric Acid/Nitrofurantoin/ CFLEX | 5.69 | 5.31 | 5.18 | 5.05 | 5.00 |
| 046-035A (Unbaked) | HEDP/Steric Acid/Nitrofurantoin/ CFLEX | 5.69 | 5.63 | 5.58 | 5.46 | 5.44 |
| 046-035B (Baked)** | Citric Acid/Ag/CFLEX | 5.69 | 4.88 | 4.84 | 4.78 | 4.79 |
| 046-035B (Unbaked) | Citric Acid/Ag/CFLEX | 5.69 | 5.41 | 5.32 | 5.19 | 5.18 |

HEDP—Hydroxy ethyl bis phosphonic acid;
PVP—Polyvinyl Phosphonic acid;
*For preparation refer to S. Sarangapani et al. Journal of Biomedical Materials research, 29, 1185–1191, (1995).
**Means that the solvent cast discs after vacuum drying were baked in a furnace at 250° C. for 5–7 minutes to mimic molding conditions.

Quick screening protocols to evaluate the efficacy of the bactericidal/bacteriostatic properties of the modified materials in comparison with the control.

The direct contact method—Contamination protocol results: In a real situation where the incontinence device carries pathogenic cells during insertion, it is necessary to ensure, as urine starts to collect or in the residual urine immediately after insertion, that the cell survival probability is reduced to zero. The protocol used examined the effect of the modified and unmodified materials in contact with about a million cells of $E.$ $coli$/mL and about 10,000 cells of Lactobacilli/mL as afunction of contact time. Both organisms were either obtained from the ATCC collection or from a hospital UTI culture collection. It also examined the survivability of the cells after 24 and 48 hour incubation. The results are shown in FIGS. 4$a$, 4$b$, 4$c$ and 4$d$.

Baked and Unbaked refer to heat treatment of the cast films at 250° C. for 15 minutes. Elaborate screening protocols to evaluate the efficacy of the bactericidal/bacteriostatic properties of the modified materials in comparison with the control were carried out in Synthetic urine as well as human urine. An $E.coli$ species from St. Joseph's Healthcare Center (Canada) isolated from an infected human was used for the adhesion study.

The results of an experiment in human urine is illustrated below. One procedure involved inoculating I mL of human urine (supplemented with 5% BHIB) with about $10^9$ cells of E.coli from a fresh overnight culture in the presence control discs and discs containing selected formulations. The mixture was vortexed and left overnight. The plate counts of apprropriate dilutions were made the next day.

The results showed that E.coli was consistently inhibited in synthetic and human urine by formulated discs (1 square centimeter) containing Citric acid and Phosphonic acids in combination with Silver. The same formulations allowed the survival of Lactobacilli (Lactobacillus GG, supplied by Dr. Gregory Reid of St. Joseph's Healthcare) in both human and synthetic urine. The human urine was always supplemented with 5% Brain Heart infusion broth (BHIB) or Tryptic Soy broth.

A complete inhibition of P. Mirabalis species HI 4320 was also significant.

TABLE IV

| Sample | E. coli | Lactobacilli |
| --- | --- | --- |
| Control blank | TNTC | TNTC |
| Control disc | 225 | TNTC |
| Sample disc containing Citric acid and Silver. | 12 | TNTC |

In general formulations containing Citric, Phosphonic acids along with Silver or Platinum were the most effective against gram negative strains. The fact that the "good bacteria" such as the Lactobacilli were not affected by the additives is clearly demonstrated.

EXAMPLE 8

This example describes the ability of the active ingredients to be blended into a polymer such as Tecoflex (Thermedics, Woburn, Mass.) an aliphatic polyurethane, as a solvent based coating. The Tecoflex resin 5% (w/v) were dissolved in THF under heat. The dissolved polymer was blended with RMA (20%) and coated onto the lumen of Tecoflex enteral feeding tubings.

A variation of this coating with pure RMA 20% w\v in THF was applied also. The THF dissolves a few layers of the polyurethane from the tubing itself and incoroporates the antibacterial on the walls.

After air drying, the coated tubes resisted clog formation over the control and showed a longevity of 45 days vs. the control that gave a longevity of 15–20 days. These experiments were carried out in an in vitro enteral feeding formula reactor simulating flow in a clinical situation. Synthetic pepsin and hydrochloric acid was also mixed at a constant rate simulating a stomach environment.

Thus, the coating of polymers containing antibacterials reduce the potential for clogging caused by bacterial biofilms.

While the foregoing invention has been described with reference to the preferred emobidments, other modifications and alterations will occur to those skilled in the art. All such modifications and alterations are intended to fall within the scope of the appended claims.

What is claimed is:

1. A coating for polymeric products used in medical applications comprising:
    a compound selected from the group consisting of aminocarboxylic acids, tricarboxylic acids, amino acids, phosphonic acids and phenolic compounds;
    a polymer; and
    silver powder having an average particle size of one micron or less.

2. The coating for polymeric products used in medical applications of claim 1 further comprising platinum black.

3. The coating for polymeric products used in medical applications of claim 2 further comprising titanium dioxide.

4. The coating for polymeric products used in medical applications of claim 1 wherein said aminocarboxylic acid is DPTA.

5. The coating for polymeric products used in medical applications of claim 1 wherein said aminocarboxylic acid is EDTA.

6. The coating for polymeric products used in medical applications of claim 1 wherein said tricarboxylic acid is citric acid.

7. The coating for polymeric products used in medical applications of claim 1 wherein said amino acid is phosphoserine.

8. The coating for polymeric products used in medical applications of claim 1 wherein said amino acid is taurine.

9. The coating for polymeric products used in medical applications of claim 1 wherein said phosphonic acid is polyvinyl phosphonic acid.

10. The coating for polymeric products used in medical applications of claim 1 wherein said phosphonic acid is hydroxy ethylidene.

11. The coating for polymeric products used in medical applications of claim 1 wherein said phenolic compound is resorcinol monoacetate.

12. A melt blended polymeric material for use in medical applications, said material comprising;
    plastic resin;
    a compound selected from the group consisting of aminocarboxylic acids, tricarboxylic acids, amino acids, phosphonic acids and phenolic compounds;
    silver powder having an average particle size of one micron or less.

13. The polymeric material of claim 12 further comprising platinum black.

14. The polymeric material of claim 13 further comprising paraben esters.

15. The polymeric material of claim 12 wherein said aminocarboxylic acid is DPTA.

16. The polymeric material of claim 12 wherein said aminocarboxylic acid is EDTA.

17. The polymeric material of claim 12 wherein said tricarboxylic acid is citric acid.

18. The polymeric material of claim 12 wherein said amino acid is phosphoserine.

19. The polymeric material of claim 12 wherein said amino acid is taurine.

20. The polymeric material of claim 12 wherein said phosphonic acid is polyvinyl phosphonic acid.

21. The polymeric material of claim 12 wherein said phosphonic acid is hydroxy ethylidene.

22. The polymeric material of claim 12 wherein said phenolic compound is resorcinol monoacetate.

* * * * *